United States Patent [19]

Everett et al.

[11] Patent Number: 5,139,033
[45] Date of Patent: Aug. 18, 1992

[54] SUTURELESS MYOCARDIAL LEAD IMPLANTATION DEVICE

[75] Inventors: Hal W. Everett, St. Paul; J. John Lattuca, Shoreview, both of Minn.

[73] Assignee: Cardiac Pacemakers, Inc., St. Paul, Minn.

[21] Appl. No.: 664,310

[22] Filed: Mar. 4, 1991

[51] Int. Cl.$^5$ .............................. A61B 5/04; A61N 1/05
[52] U.S. Cl. ..................................... 128/785; 128/642
[58] Field of Search ................ 128/784–786, 128/419 P, 642; 606/32

[56] References Cited

U.S. PATENT DOCUMENTS

| | | |
|---|---|---|
| 3,078,850 | 2/1963 | Schein et al. ............ 128/419 P |
| 3,875,947 | 4/1975 | Jula et al. |
| 4,144,890 | 3/1979 | Hess . |
| 4,146,037 | 3/1979 | Flynn . |
| 4,207,903 | 6/1980 | O'Neill . |
| 4,209,019 | 6/1980 | Dutcher . |
| 4,235,246 | 11/1980 | Weiss . |
| 4,258,724 | 3/1981 | Balat et al. ............ 128/785 |
| 4,271,846 | 6/1981 | Little . |
| 4,280,510 | 7/1981 | O'Neill . |
| 4,280,512 | 7/1981 | Karr et al. ............ 128/785 |
| 4,280,513 | 7/1981 | Gilbert . |
| 4,299,239 | 11/1981 | Weiss et al. . |
| 4,424,818 | 1/1984 | Doring et al. . |
| 4,624,266 | 11/1986 | Kane . |
| 4,646,755 | 3/1987 | Kane . |
| 4,913,151 | 4/1990 | Harui et al. ............ 28/642 |
| 4,972,847 | 11/1990 | Dutcher et al. ............ 128/785 |
| 5,036,854 | 8/1991 | Schollmeyer et al. ............ 128/785 |
| 5,040,545 | 8/1991 | Dutcher . |

FOREIGN PATENT DOCUMENTS 2830412 1/1980 Fed. Rep. of Germany ...... 128/642

Primary Examiner—Lee S. Cohen
Assistant Examiner—Krista M. Pfaffle
Attorney, Agent, or Firm—Haugen and Nikolai

[57] ABSTRACT

A sutureless myocardial positive fixation lead implantation device is disclosed. An inner plastic rod is encased in an outer plastic sleeve. The outer plastic sleeve is affixed to a handle in which a central bore has been introduced. The inner rod is of sufficient length that a small length extends proximally from the handle when it is positioned within this bore, and it simultaneously extends the full length of the outer plastic sleeve. A suction cup is affixed to the distal end of the outer plastic sleeve. A holder means for receiving the proximal end of a typical myocardial lead is affixed to the handle to ensure that the lead is held taut and, thus, prevents entanglement during use.

A specially designed smooth electrode head is pressed against the suction cup so that a lead having a corkscrew shaped electrode projecting from the head can be held by the device while it is rotated into place. Pressure exerted on the proximal end of the inner rod presses the distal end of the rod against the top of the suction cup and is used to break the suction and release the lead head. This process is reversible, so the electrode can be moved and reinstalled at another site.

5 Claims, 1 Drawing Sheet

SUTURELESS MYOCARDIAL LEAD IMPLANTATION DEVICE

BACKGROUND OF THE INVENTION

I. Field of the Invention

This invention relates generally to instruments for facilitating the placement of electrical stimulating/sensing leads in the body of a patient and more particularly to an improved device for the affixation of a sutureless electrode on such a lead to cardiac tissue.

II. Discussion of the Prior Art

Medical electrode placement directly upon or within myocardial (heart) tissue is commonplace, and many medical electrode placement systems have been devised to assist in attaining accurate placement. However, as will be set forth in greater detail below, these systems share a common problem. Many of them utilize the principle of grasping an insulating head from which the electrode projects with an introducer, positioning the electrode appropriately, then releasing the head and withdrawing the tool. The problem is that the relatively bulky head remains. Other lead designs utilize an internal clamping mechanism to avoid this problem, but they still have other bulky projections on their surface.

A typical prior art cardiac stimulating lead comprises an elongated lead body having a proximal and distal end. The lead body includes one or more flexible electrical conductors contained within a pliable, flexible insulating sheath. Suitable connectors are affixed to the proximal end of the conductors for facilitating attachment to an implantable or external electrical stimulating pulse generator. Affixed to the distal end of the lead body are one or more electrodes which are joined to the embedded conductor(s).

One known type of stimulating lead is the so-called myocardial screw-in lead. In this arrangement, one of the electrodes comprises a rigid helix having spaced-apart convolutions. It is supported by a molded plastic head, with the helix projecting perpendicularly from a surface of the head. The lead is installed using a specially designed tool which frictionally grasps the lead head, allowing the helix to be rotated into and be anchored by the tissue to be stimulated. Thus, the tool is used much like a screw driver. The head from which the electrode protrudes often includes irregular protuberances with which the insertion tool is intended to cooperate. This irregular surface may rub against tissue. Eventually, the rubbing can create severe medical problems for the patient, examples of which are common in the medical literature. These involve both sutured and sutureless electrodes.

The present invention obviates the need to avoid electrodes that have extensions or other protrusions on their upper surface. Unfortunately, prior art approaches to the releasible introduction of myocardial electrodes have relied either upon grasping such extensions or protrusions, or upon dimensioning the electrode to permit internal grasping, requiring a bulky electrode head.

An example of an electrode that requires a forceps-like device for insertion is disclosed in U.S. Pat. No. 4,144,890 of Hess. Forceps are used to flex the electrode body into a concave posture. The surface prongs are inserted into the myocardium, then the forceps are released. Distension of the electrode body firmly anchors the surface prongs within the tissue. Necessarily, then, the electrode head must be dimensioned to receive the forceps, which results in a potentially abrasive shape.

A lead installation tool utilizing a releasable clamp that mates with an electrode mounting head is disclosed in U.S. Pat. No. 4,271,846 of Little. A specially-designed electrode head has a groove into which an abutment fits until the corkscrew electrode is properly placed in the myocardium. A clamp operator conductor carrier assembly then moves the clamp into a release position, and the installation tool can then be removed from the field. Although the upper edge of this electrode is rounded, the edges defined by the groove may rub against tissue such as the atrial appendage, causing damage.

An alternative introducer tool is disclosed in U.S. Pat. No. 4,646,755 of Kane. Using an insertable stylet that is fed through the lumen of an electrode lead, this tool includes a plunger housing. The plunger housing shifts within a locking tube to engage the tool in an advanced or a retracted position. When in the advanced position, clamping elements on this plunger housing engage the stylet to prevent movement. Thereupon, the lead may be rotated about the stylet in relation to the introducer tool in order to affix the helical attachment assembly on the electrode surface within tissue.

It is accordingly a principal object of the present invention to provide a new and improved apparatus for affixing sutureless myocardial leads to cardiac tissue.

It is another object to permit the use of lead head that is smoother, rounded and void of sharply edged surfaces and thus less irritating to tissue, particularly in pediatric patients.

Another object is to avoid erosion through surrounding tissues due to lead irritation.

SUMMARY OF THE INVENTION

The implantation device of the present invention permits sutureless myocardial leads to be reversibly affixed to tissue. It consists of a tubular member having a hand grip at its proximal end and a distal suction cup which cooperates with a smoothly rounded electrode-supporting lead head when attaching a lead to heart or other tissue.

The hand grip segment of the installation instrument has a proportionately wide cylinder of rigid plastic for ease of gripping. A central bore, which runs the length of the tubular member, permits placement of an inner rod within the cylinder. The bore and rod are closely dimensioned so that longitudinal displacement of the rod is possible, but sufficient tension is retained to prevent the rod from freely slipping. The hand grip segment further includes a lead body clamping bracket mounted to the side of the rigid plastic cylinder, which receives the proximal end of a myocardial lead and retains it taut to permit the lead and the insertion tool to be rotated as a unit without twisting the lead.

Affixed to the distal end of the tubular member is a rubber suction cup having a concave surface facing in the distal direction. The suction cup is dimensioned to conform to a smoothly-rounded, dome-shaped protuberance on the molded head of the lead from which the rigid conductive electrode helix projects.

In operation, the lead head carrying the electrode is pressed into the suction cup and securely held by suction. The proximal end of the lead is fitted into the clamping bracket attached to the hand grip. The instrument is positioned over a desired implantation site and rotated clockwise, allowing the rigid helix of the electrode to fully embed itself in tissue. Now, by gripping the handle and depressing the proximal end of the inner rod that extends above the proximal surface of the handle with the thumb, the rod is pushed against the suction cup causing the central region of the suction cup to progressively deform until the suction is broken and the electrode head is released. The proximal end of the lead is then withdrawn from the lead body clamping bracket and is subsequently mated with a pulse generator.

If it is desired that the embedded electrode be moved from its present position, the proximal end of the inner rod of the implantation device is partially depressed, and the suction cup is placed over the domed protuberance of the molded head holding the electrode. Releasing the pressure on the inner rod creates a vacuum which again adheres the suction cup to the domed head. Subsequently, the proximal end of the lead may be reintroduced into the clamping bracket on the handle. The handle can then be rotated counterclockwise, and the electrode removed and repositioned or discarded.

The foregoing objects and advantages of the invention are achieved by providing a suction-based electrode placement device for the implantation of sutureless myocardial leads. This permits the attachment and removal of lead systems that use a smooth surfaced electrode head instead of one with potentially irritating projections.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE PREFERRED EMBODIMENT

Figure 1:
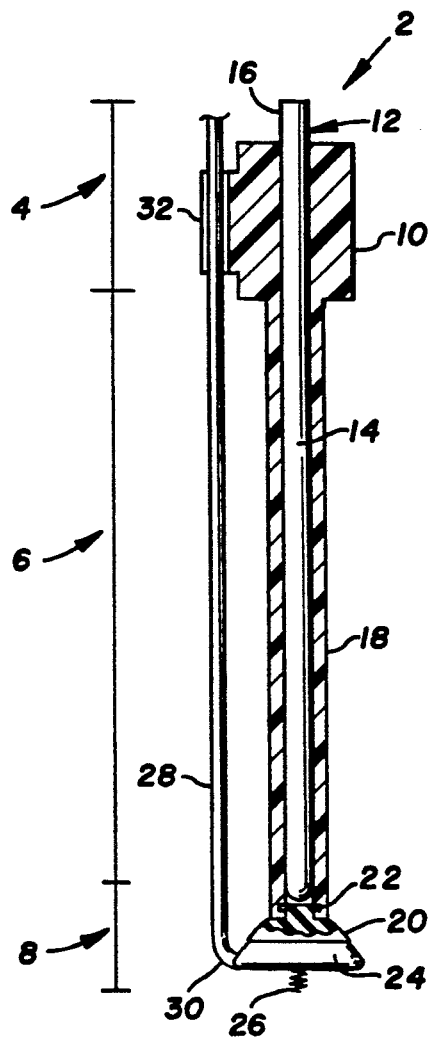
FIG. 1 depicts a cross-sectional view of a preferred embodiment of the present invention.

A preferred embodiment of the sutureless lead implantation device of the present invention is shown in FIG. 1. It features a suction cup device designed to releasably hold a rounded electrode lead head, thus avoiding the use of prior art angularly shaped electrode lead heads.

Referring to FIG. 1, the sutureless lead insertion instrument 2 is seen to be comprised of a hand grip segment 4, a tubular extension 6 and a suction cup portion 8. The hand grip segment 4 has a handle 10, preferably composed of hard plastic having a knurled surface for ease of gripping. A central hole 12 is bored through hand grip 4. An inner cylindrical plastic rod 14 is inserted through the bored hole 12 and is dimensioned to a length such that a short length 16 thereof extends proximally from the handle and extends distally the full length of the tubular extension 6. The inner plastic rod 14 is preferably made of a stiff but somewhat flexible material, such as polyethylene. The outer plastic sleeve 18 is integrally formed with or permanently affixed to the knurled handle 10, so that torquing the handle 10 will also rotate the outer plastic sleeve 18. Affixed to the distal end of the outer plastic sleeve 18 is a flexible suction cup 20. It is held in place by expansion forces exerted against the inner surface of sleeve 18 by the rubber suction cup 20 at lip 22 fitting into an annular groove formed in the wall of the bore 14.

Figure 2:
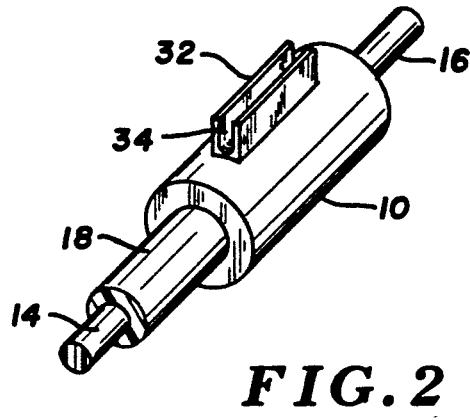
FIG. 2 depicts a side view of the lead body clamping bracket of the present invention.

The concave portion of suction cup 20 is dimensioned to precisely fit the rounded head 24 of the lead. The head 24 has a helical positive fixation means (corkscrew 26), as known in the art. When the lead head is twisted, the helix 26 is screwed into the tissue and anchors itself at a selected site of the myocardial tissue. The distal end of an elongated conductor in the lead body 28 is permanently affixed at 30 to the helical electrode 26 within the lead head 24. A lead body clamping bracket 32 is rigidly affixed to the handle 10. The lead body clamping bracket 32 may comprise a block of plastic having a U-shaped channel 34 formed therein and it is adapted to receive the proximal end of the lead 28. It assists in stabilizing the lead 28 so that it does not twist or become entangled as the implantation device 2 is rotated about its longitudinal axis. A side view illustrating the dimensioning of the lead body clamping bracket 32 is shown in FIG. 2. The bracket 32 is rigidly mounted upon the knurled handle 10. An U-shaped channel 34 is molded or routed in bracket 32 to receive the proximal end of the lead 28. It is dimensioned to securely hold the lead 28 without exerting such pressure on its walls that the enclosed elongated conductor (not shown) is crushed or otherwise damaged.

To affix an electrode 26 and lead 28 using the sutureless lead implantation device 2 of the present invention, the rounded top of the lead head 24 is pushed against the flexible suction cup 20 until all air is expelled, creating a vacuum. Lead 28 is fed alongside the outer plastic sleeve 18, until its end reaches the lead body clamping bracket 32. This end is inserted into the U-shaped channel 34 in lead body clamping bracket 32, described in further detail hereinafter, until the lead 28 is relatively taut between the bracket 32 and the head 24. The entire assembly 2 is then introduced through a thoracotomy space and an open pericardium so that the electrode 26 is positioned exactly over the desired site on the heart. Once a site on the heart is selected, the helical electrode 26 is pressed against the myocardium and the entire assembly 2 is rotated clockwise. The helix 26 is thus inserted to the desired depth, then rotation is arrested.

Figure 3:
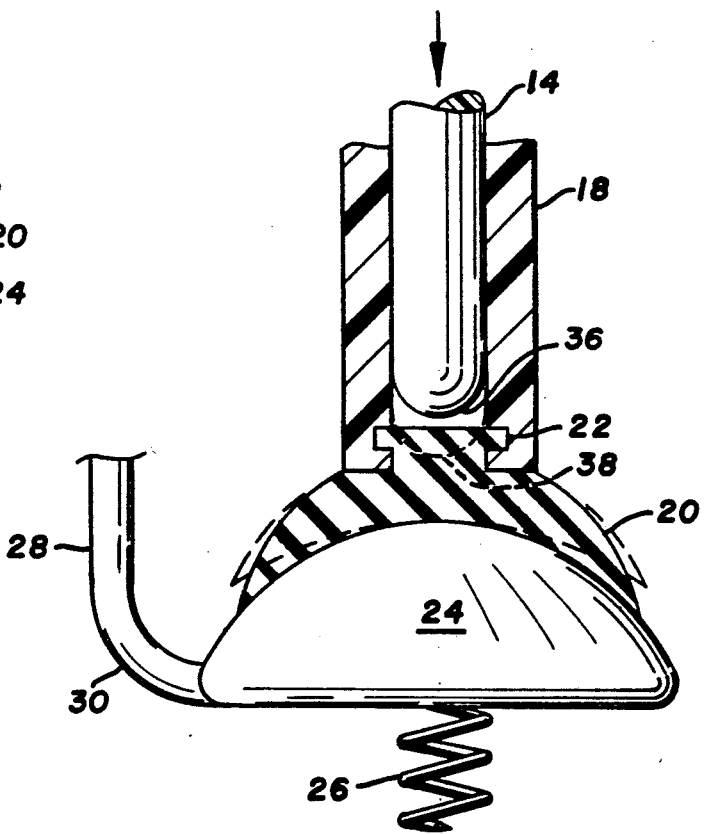
FIG. 3 depicts the release mechanism of the preferred embodiment of the present invention.

FIG. 3 demonstrates release of the lead head 24 and lead 28 from the lead holder 2. Downward thumb pressure is exerted on the proximally extending portion 16 of the inner rod 14 forcing its distal end against the juxtaposed surface of the suction cup 20. Thus, from the initial position shown by dashed lines 36, the inner rod 14 pushes against the central region on the convex side of flexible suction cup 20 until it deforms this region. It increasingly presses against lead head 24, first stretching the undersurface of the suction cup 20. When the rod 14 reaches a position approximated by position 38, it breaks the vacuum between the inner surface of the suction cup 20 and the outer surface of the domed lead head 24, thus releasing the lead head 24. Grasping and pulling the portion of the lead 28 entrapped in channel 34 will free the lead from the lead body clamping bracket 32. The holder is then removed from the chest cavity and the remainder of the medical procedure being performed continues.

If it becomes necessary to move the electrode to a new site on the myocardium, the top portion 16 of the inner rod 14 is simply depressed toward handle 10 to stretch the central concave undersurface of the suction cup 20. The implantation device 2 is positioned directly over the head 24 of lead 28, then the suction cup 20 is placed on the rounded dome of the lead head 24. When the pressure is released from the top 16 of the inner rod 14, a vacuum is again created, binding the suction cup 20 to the lead head 24. The implantation device 2 can then be rotated counterclockwise, unscrewing the helical electrode 26 from the myocardial tissue. A new site can be selected, and then the introduction procedure is repeated.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. An insertion tool for installing a positive fixation cardiac stimulation lead of the type comprising an elongated flexible insulated conductor having a proximal end and a distal end, said distal end connected to a rigid open conductive helix, said helix projecting from an insulative head member, said head member having a smooth surface, said tool comprising:
   (a) a rigid cylindrical, elongated handle;
   (b) a suction cup member affixed to one end of said rigid handle, said suction cup member having a concave surface conforming to said smooth surface of said head member;
   (c) means affixed to said handle for retaining said insulated conductor adjacent the length of said elongated handle when said suction cup member grips said smooth surface of said head member; and
   (d) means for selectively breaking a vacuum between said suction cup member and said smooth surface of said head member from a location remote from said suction cup member.

2. The insertion tool as in claim 1 wherein said rigid cylindrical handle is a tube having a central bore extending the length thereof and wherein said means for selectively breaking further includes a rigid rod slidingly disposed in said central bore, said rod being longer than the length of said handle.

3. The sutureless myocardial lead implantation device of claim 1, wherein said rigid cylindrical, elongated handle is comprised of a rigid plastic.

4. The insertion tool of claim 1, wherein said suction cup member is formed from an elastomeric material.

5. A method of attaching a positive fixation cardiac stimulating lead to a living heart comprising the steps of:
   (a) providing a positive fixation lead having a rigid, helical electrode projecting normally from a lead head, said lead head having a smooth surface;
   (b) providing a lead insertion tool having an elongated rigid tubular handle with a proximal end and a distal end, there being a suction cup affixed to said distal end and a rigid rod extending through the center of said tubular handle and projecting beyond said proximal end;
   (c) pressing said suction cup against said smooth surface to create a vacuum therebetween;
   (d) positioning said helical electrode against the heart while rotating said handle to screw said helical electrode into said heart; and
   (e) depressing the exposed end of said rigid rod to distort said suction cup to the point of breaking the vacuum.

* * * * *